United States Patent
Madabhushi et al.

(10) Patent No.: US 9,424,460 B2
(45) Date of Patent: *Aug. 23, 2016

(54) TUMOR PLUS ADJACENT BENIGN SIGNATURE (TABS) FOR QUANTITATIVE HISTOMORPHOMETRY

(71) Applicant: Case Western Reserve University, Cleveland, OH (US)

(72) Inventors: Anant Madabhushi, Beachwood, OH (US); George Lee, Parlin, NJ (US); Sahirzeeshan Ali, Houston, TX (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/590,082

(22) Filed: Jan. 6, 2015

(65) Prior Publication Data

US 2015/0254493 A1    Sep. 10, 2015

Related U.S. Application Data

(60) Provisional application No. 61/950,357, filed on Mar. 10, 2014.

(51) Int. Cl.
| | |
|---|---|
| *G06K 9/00* | (2006.01) |
| *G06T 11/20* | (2006.01) |
| *G06F 19/00* | (2011.01) |
| *G06T 7/00* | (2006.01) |
| *G06K 9/46* | (2006.01) |
| *C40B 30/06* | (2006.01) |

(52) U.S. Cl.
CPC ............ *G06K 9/0014* (2013.01); *G06F 19/345* (2013.01); *G06K 9/469* (2013.01); *G06T 7/0012* (2013.01); *G06T 11/203* (2013.01); *G06T 11/206* (2013.01); *G06T 2207/10056* (2013.01); *G06T 2207/20076* (2013.01); *G06T 2207/30024* (2013.01)

(58) Field of Classification Search
USPC ....... 382/100, 103, 106, 128–134, 151, 162, 382/168, 170, 173, 181, 190, 199, 203, 219, 382/224, 232, 254, 266, 274, 276, 286–291, 382/305, 312; 506/9, 10; 424/9.1; 378/4, 21
See application file for complete search history.

(56) References Cited

U.S. PATENT DOCUMENTS

| | | | | |
|---|---|---|---|---|
| 2010/0177950 | A1* | 7/2010 | Donovan | G06F 19/3437 382/133 |
| 2010/0298166 | A1* | 11/2010 | Alon | A61K 31/4745 506/10 |
| 2012/0245045 | A1* | 9/2012 | Kislin | C12N 15/113 506/9 |
| 2013/0101513 | A1* | 4/2013 | Yang | A61B 5/0059 424/9.1 |
| 2014/0294279 | A1* | 10/2014 | Madabhushi | G06T 7/0014 382/133 |

\* cited by examiner

*Primary Examiner* — Seyed Azarian
(74) *Attorney, Agent, or Firm* — Eschweiler & Associates, LLC

(57) ABSTRACT

Methods, apparatus, and other embodiments associated with predicting prostate cancer (CaP) progression using tumor cell morphology features and benign region graph features are described. One example apparatus includes a set of logics that acquires an image of a region of tissue, detects and segments cells in the image, extracts a set of morphological features from cells in a first region in the image, constructs a graph of a localized cellular network in a second region of the image, extracts a set of graph features from the graph, generates a set of tumor plus adjacent features signature (TABS) features from the sets of graph features and the set of morphological features, and calculates the probability that the image is a progressor or non-progressor based, at least in part, on the set of TABS features. The first region may concern cancerous cells and the second region may concern benign cells.

30 Claims, 5 Drawing Sheets

TUMOR PLUS ADJACENT BENIGN SIGNATURE (TABS) FOR QUANTITATIVE HISTOMORPHOMETRY

CROSS REFERENCE TO RELATED APPLICATIONS

This application claims the benefit of U.S. Provisional Application 61/950,357 filed Mar. 10, 2014.

BACKGROUND

Tens of thousands of prostate cancer (CaP) patients undergo radical prostatectomies (RP) in the United States each year. Despite the effectiveness of RP in treating CaP, 15% to 40% of men will experience, following RP, disease progression manifested as biochemical recurrence, local or distant cancer recurrence, or cancer death. The Gleason sum (GS) is a measure used by pathologists to assess tissue morphology. In Gleason scoring, the two most common Gleason patterns are scored on a scale of 1 to 5. The sum of the two scores is the Gleason Sum, which ranges from 2 through 10 and is the conventional method of predicting CaP progression. High GS cases are correlated with cancer progression. Patients with high GS may be provided with more aggressive secondary treatments in addition to RP. GS is, however, only associated with cancerous foci. Conventional methods of cancer grading that use only GS are unable to grade patterns in benign stromal areas proximal to cancer foci.

Pathologists have conventionally used microscopes to conduct visual evaluation of histological tissue. Manual evaluation of histological tissue is excessively time consuming in a clinical environment, and may suffer from poor inter-interpreter agreement. Digital whole slide scanners have enabled automated evaluation of histological tissue through quantitative histomorphometry (QH). Conventional QH methods have used nuclear shape as a predictor of CaP. Other conventional QH methods have used nuclear roundness variance to evaluate the tumor area of prostate tissue for CaP progression with greater effectiveness than traditional Gleason scoring.

Some conventional methods have demonstrated the field effect through higher nuclear morphometric scores associated with benign prostate nuclei found near tumor regions. However, conventional methods that investigate benign prostate nuclei use Feulgen-staining of DNA, which is not a standard staining technique employed by pathologists investigating CaP. Thus, conventional methods for predicting CaP progression that rely on just GS use only the tumor tissue to gather information about morphological features. Conventional methods that attempt to gather information from benign regions use non-standard staining techniques that pathologists may not be trained to analyze. The use of non-standard staining techniques may increase the time required to implement those methods, and reduce the accuracy of those methods.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
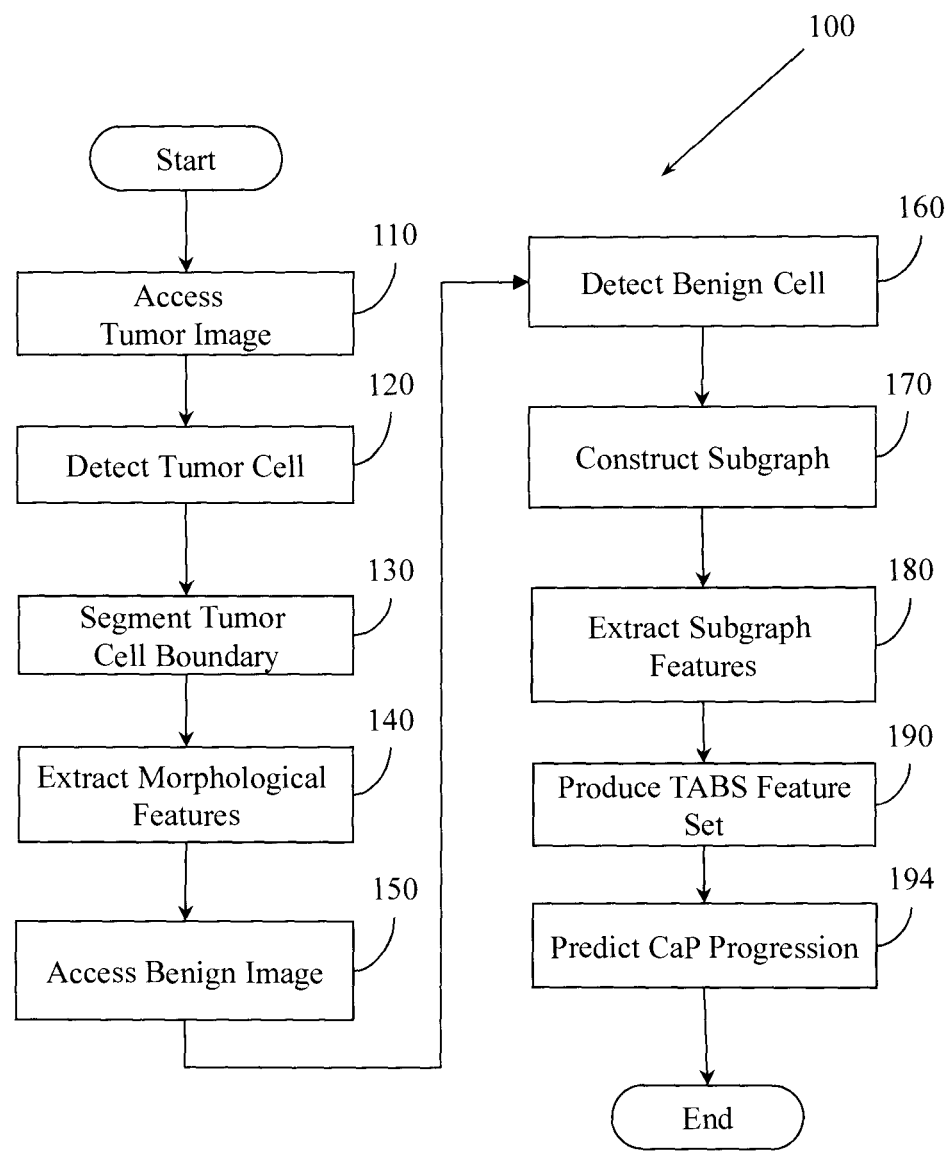
FIG. 1 illustrates an example method of predicting CaP progression in a patient using field effects in automated QH.

Nearly 75,000 radical prostatectomies are performed each year in the United States to treat CaP. After undergoing RP, up to 40% of patients will experience disease progression manifested as biochemical recurrence, local or distant cancer recurrence, or death. Improving the accuracy with which CaP progression may be predicted has the concrete and tangible result of increasing treatments and resources directed to those patients more likely to suffer CaP progression, and reducing un-needed treatments and resources directed towards those patients unlikely to suffer CaP progression.

Conventional methods for predicting CaP progression typically employ Gleason scoring. The Gleason Sum (GS) is a measure used by pathologists to assess tissue morphology. High GS score cases are correlated with cancer progression. Patients with high GS scores may be provided with more aggressive secondary treatment in conjunction with RP. Patients with lower GS scores may be provided with less aggressive treatments. Conventional methods that employ the GS traditionally involve a human pathologist using a microscope to make a visual evaluation of a section of histological tissue. Digital whole slide scanners have allowed the development of QH for automated evaluation of histological tissue to complement manual pathologist evaluation. QH allows automated evaluation of nuclear shape in cancerous tissue as a predictor for CaP. QH also enables automated evaluation of nuclear roundness variance among cancerous nuclei in the tumor area, which, in some cases, results in better accuracy than Gleason scoring when predicting CaP progression. However, conventional methods that employ QH and GS do not leverage the field effect associated with benign prostate nuclei found near tumor regions.

The field effect describes the micro-environment around the site of a tumor that may lead to a progression of the disease at another site. Predicting CaP progression using the field effect involves analyzing the benign stromal tissue found adjacent to cancerous tissue. Higher nuclear morphometric scores for benign prostate nuclei near tumor regions indicate that there are visual cues that may serve as markers for disease progression from within the benign regions. Conventional methods for analyzing the field effect in benign regions use Feulgen-staining of DNA rather than standard H&E stained slides. Pathologists are more likely to be familiar with H&E stained slide analysis than with Feulgen DNA staining. Thus, conventional methods of analyzing the field effect are not clinically optimal, since a pathologist would have to undergo costly and time-consuming training to learn how to implement Feulgen-stained DNA analysis.

Example methods and apparatus predict CaP progression using cell graph features extracted from H&E stained slides of benign regions along with nuclear morphological descriptors obtained from cancer regions. Example methods and apparatus construct a cell graph of a benign region surrounding or adjacent to a tumor area. Example methods and apparatus extract a set of graph features from the graph of the benign region. Example methods and apparatus extract a set of morphological features from tumor cells. Example methods and apparatus select the features from each set that are most prognostically informative for predicting CaP progression. The top selected features are combined into a tumor plus adjacent benign signature (TABS) set of features. The TABS set of features may be employed with Gleason scoring to identify with greater accuracy than conventional methods CaP patients who will experience disease progression following RP. For example, while conventional features obtained from cancerous tissue sections show a predictive area under the curve (AUC) of at best 0.72, example methods and apparatus add features obtained from the benign regions and increase the AUC to 0.74. When example methods and apparatus employ TABS along with GS, the AUC increases to at least 0.82. By increasing the accuracy with which CaP progression is predicted, example methods and apparatus produce the concrete, real-world result of increasing the probability that at-risk patients receive timely treatment, and reducing the expenditure of resources and time on patients who are less likely to demonstrate CaP progression. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a computerized method 100 of predicting CaP progression in a patient using field effects in automated quantitative histomorphometry (QH). Method 100 includes, at 110, accessing a first digital image of a cancerous section of a prostate that demonstrates pathology associated with CaP in the patient. In one embodiment, the first digital image is of a section of tumor tissue. Accessing an image includes acquiring electronic data, reading from a computer file, receiving a computer file, reading from a computer memory, or other computerized activity. In one embodiment, the first digital image may be a tissue microarray (TMA) image. More generally, the digital image is a digital image of a tissue slide. In one embodiment, the image is a 1670 pixel by 1670 pixel image of a 0.6 mm tissue microarray core stained with H&E. In one embodiment, the image may be acquired by scanning the image from a high power field (HPF) of an H&E stained tissue slide. In this embodiment, the image is acquired using a slide scanner and a multi-spectral microscope. The slide-scanner may be, for example, an Aperio XT scanner. In other embodiments, the image may have different dimensions and may be acquired from other systems. In still other embodiments, the image may represent a different sized tissue microarray core, or the microarray core may be stained with a different technique.

FIG. 1 also includes, at 120, detecting a first cell in a first region of interest of the first digital image. In one embodiment, the first cell is a tumor cell detected in a tumor region of the first digital image. The tumor region of the first digital image is distinguishable from a benign region of the first digital image. The first cell is detected using a shape-based active contour segmentation scheme.

FIG. 1 also includes, at 130, segmenting the boundary of the first cell into a set of cell boundary points. The first cell boundary is segmented using the shape-based active contour segmentation scheme. The segmentation scheme includes an energy functional of the active contour.

In one embodiment, the energy functional has three terms. The energy functional may be defined as $F=\beta_s+\int_\Omega (\phi(x)-\psi(x))^2 |\nabla\phi|\delta(\phi)dx + \beta_r\int_\Omega \theta_{in}H_\psi dx + \int_\Omega \theta_{out}H_{-\psi}dx$. In this embodiment, the first term $\beta_s\int_\Omega(\phi(x)-\psi(x))(\phi(x)-\psi(x))^2|\nabla\phi|\delta(\phi)dx$ represents a shape plus boundary force. The shape plus boundary force is a prior shape term modeled on a prostate cell nucleus. The shape plus boundary force constrains the deformation achievable by the active contour. In another embodiment, the prior shape term may be modeled on a cell nucleus other than a prostate cell nucleus.

The energy function has a second term and a third term. The second and third terms represent a region force. The second term, $\beta_r\int_\Omega \theta_{in}H_\psi dx$, is a boundary-based term that detects nuclear boundaries from image gradients. The third term, $\int_\Omega \theta_{out}H_{-\psi}dx$, drives the shape prior and the contour towards the nuclear boundary based on region statistics.

In this embodiment, $\beta_s, \beta_r > 0$ are constants that balance contributions of the shape plus boundary force and the region force. $\{\phi\}$ is a level set function. $\psi$ is a shape prior. $\delta(\phi)$ is a contour measure on $\{\phi=0\}$. $H(.)$ is the Heaviside function. $\theta_r = I/-u_r|^2 + \mu|\nabla u_r|^2$, where $r\in\{in, out\}$. $u_r$ is defined such that $r\in\{in, out\}$ are partitioned foreground and background regions. $\Omega$ is a bounded open set in $\mathbb{R}^2$.

Method 100 also includes, at 140, extracting a set of morphological features from the set of cell boundary points.

In one embodiment, method 100 extracts a set of at least morphological features based on the segmentation of the boundary of the first cell into a set of cell boundary points. Extracting the set of morphological features from the set of cell boundary points includes calculating a set of morphological features based, at least in part, on statistics related to the set of cell boundary points. These statistics include nuclear area and smoothness. In another embodiment, a different number of morphological features may be extracted based on statistics other than nuclear area and smoothness.

Method 100 also includes, at 150, accessing a second digital image of a benign section of the prostate. In one embodiment, the second digital image of the benign section of the prostate is an image of a section of a benign region of the prostate located adjacent to the tumor region of the prostate. The benign region is distinguishable from the tumor region. In another embodiment, the second digital image of the benign section of the prostate is acquired from the same section of tissue as the digital image of the tumor region of the prostate. In one embodiment, the second digital image may be a TMA image.

Method 100 also includes, at 160, detecting a second cell in a second region of interest in the second digital image. In one embodiment, the second cell is detected using the shape-based active contour segmentation scheme. In another embodiment, the cell may be detected using a different segmentation scheme.

Method 100 also includes, at 170, constructing a subgraph of a localized cell network within the second region of interest. Example apparatus and methods extract features from benign tissue regions adjacent to tumor regions using localized subgraphs. Nodes of the subgraph represent individual cell nuclei centroids. Edges of the subgraph are defined between pairs of nodes by a probabilistic decaying function. A subgraph $G=\{V, E\}$ is defined where V represents the set of n nuclear centroids $\gamma_i, \gamma_j \epsilon V$. Nodes are defined as $i, j \epsilon \{1, 2, \ldots, n\}$. E represents the set of edges that connect the nodes in the subgraph G. The edges between the pairs of nodes $\gamma_i, \gamma_j$ are set as a probabilistic decaying function $$E=\{(i,j): r<d(i,j)^{-\alpha}, \forall \gamma_i, \gamma_j \epsilon V\}$$

where $d(i,j)$ represents the Euclidean distance between nodes $\gamma_i$ and $\gamma_j$. The density of the graph is controlled by $\alpha > 0$. Values of $\alpha$ approaching 0 indicate a high probability of connecting nodes. Values of $\alpha$ approaching infinity indicate a low probability of connecting nodes. $r \epsilon [0, 1]$ is an empirically determined edge threshold. In one embodiment, $r \epsilon [0, 1]$ may be generated by a random number generator.

Method 100 also includes, at 180, extracting a set of subgraph features from the subgraph. The set of subgraph features characterizes a field effect of the local cell organization. For example, a benign non-progressor may display a sparser arrangement of cells visible in a graph than a benign core of a progressor. Subgraphs that capture the different arrangements between progressors and non-progressors enable automated QH to predict disease progression based on the properties of the benign tissue. By employing H&E stained slides, method 100 improves on conventional methods that employ Feulgen-staining of DNA.

In one embodiment, the set of subgraph features includes at least 26 features. The set of subgraph features includes eccentricity and connected component size. In another embodiment, other features, and other numbers of features, may be extracted.

Method 100 also includes, at 190, producing a set of TABS features from the set of morphological features and the set of subgraph features. In one embodiment, producing the set of TABS features includes selecting at least a threshold number of the most prognostically informative features for predicting CaP progression from the set of morphological features and from the set of subgraph features. For example, 7 nuclear subgraph features, 1 nuclear morphology feature, and 1 nuclear density feature may be the most prognostically informative features extracted from the benign region. Similarly, 9 nuclear morphology features and 1 Delaunay triangulation may be the most prognostically informative features extracted from the tumor region. In this example, the combined TABS feature set may include 7 nuclear subgraph features from the benign region, 1 nuclear morphology feature from the tumor region, 1 Delaunay triangulation from the tumor region, and 1 nuclear morphology feature from the benign region. In one embodiment, the threshold number is 10, and the threshold number of features are selected using a Wilcoxon Rank Sum test. In other embodiments, other numbers of features may be selected, and other tests, including other non-parametric tests of the null hypothesis, may be used to select the threshold number of features.

Method 100 also includes, at 194, controlling a computer to predict CaP progression in the patient, based, at least in part, on the set of TABS features. In one embodiment, a computer aided diagnostic system (CADx) is controlled by method 100 to calculate a probability that the digital image under analysis represents a progressor or a non-progressor. The CADx calculated probability may then be employed to complement a human pathologist's determination that the digital image represents a progressor or a non-progressor.

Improved prediction of CaP progression using automated QH may produce the technical effect of improving treatment efficacy and improving doctor efficiency by increasing the accuracy and decreasing the time required to predict CaP progression. Treatments and resources may be more accurately tailored to patients with more aggressive cancer so that more appropriate protocols may be employed. Using a more appropriate protocol may lead to less therapeutics being required for a patient or may lead to avoiding or delaying a resection or other invasive procedure. When CaP progression is more quickly and more accurately detected, patients most at risk may receive a higher proportion of scarce resources (e.g., therapeutics, physician time and attention, hospital beds) while those less at risk may be spared unnecessary treatment, which in turn spares unnecessary expenditures and resource consumption. Example methods and apparatus may also have the concrete effect of improving patient outcomes.

While FIG. 1 illustrates various actions occurring in serial, it is to be appreciated that various actions illustrated in FIG. 1 could occur substantially in parallel. By way of illustration, a first process could detect and segment cellular boundaries in the first digital image, a second process could construct a subgraph, and a third process could construct a set of TABS features. While three processes are described, it is to be appreciated that a greater or lesser number of processes could be employed and that lightweight processes, regular processes, threads, and other approaches could be employed.

Figure 2:
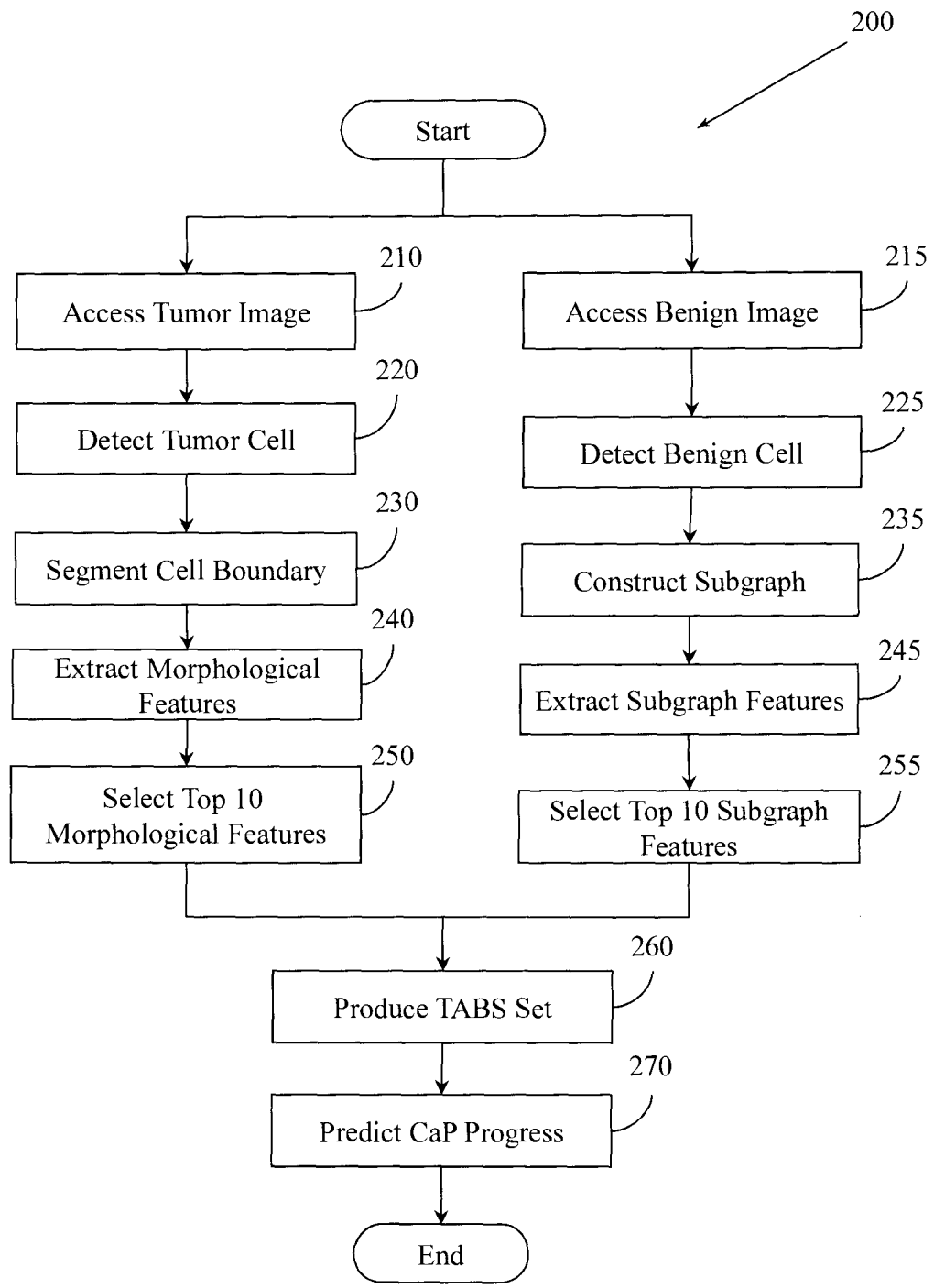
FIG. 2 illustrates an iteration of a method associated with predicting CaP progression in a patient using field effects in automated QH.

FIG. 2 illustrates an iteration of a method 200 associated with predicting CaP progression in a patient using field effects in automated QH. Method 200 is similar to method 100, but the embodiment illustrated in FIG. 2 shows method 200 operating in parallel, instead of serially, as method 100 is illustrated in FIG. 1. Method 200 includes, at 210, accessing an image of a tumor region of a section of prostate tissue. Method 200, at 220, detects a tumor cell in the image.

At 230, method 200 segments the cell boundary of the tumor cell into a set of cell boundary points. In one embodiment, method 200 uses a shape-based active contour segmentation scheme to detect and segment the tumor cell. Method 200 also includes, at 240, extracting a set of morphological features from the set of cell boundary points. Method 200 also includes, at 250, selecting the top ten morphological features from the set of morphological features. The top ten morphological features are the ten most prognostically informative morphological features. Method 200 may select the top ten most prognostically informative features from the set of morphological features using a Wilcoxon Rank Sum test. Method 200 may also calculate Delaunay triangulation features or Voronoi polygon area features from the tumor image and these features may be included in the top ten morphological features. In another embodiment, more or less than ten features may be selected.

Method 200 also includes, at 215, accessing an image of a benign region of the prostate. Method 200, at 225, detects a benign cell in the image. In one embodiment, method 200 uses a shape-based active contour segmentation scheme to detect the benign cell. Method 200, at 235, constructs a subgraph of a localized cellular network in the benign region of the prostate represented in the benign image. The nodes of the subgraph represent individual cell nuclei centroids. The edges of the subgraph are defined by a probabilistic decaying function of the Euclidean distance between a pair of nodes. The density of the subgraph is user-adjustable. Method 200, at 245, extracts a set of subgraph features from the subgraph. The set of subgraph features may include statistics of Voronoi polygon area, Delaunay edge length, or nuclear density features that describe the clustering of nuclei. In another embodiment, other features may be extracted from the subgraph. Method 200 also includes, at 255, selecting the top ten subgraph features from the set of subgraph features. The top ten subgraph features are the ten subgraph features that are most prognostically informative for predicting CaP progression. The top ten subgraph features are selected, in one embodiment, using a Wilcoxon Rank Sum test. In another embodiment the top ten subgraph features may be selected using a different technique. In another embodiment, more or less than ten subgraph features may be selected.

In method 200, steps 210, 220, 230, 240, and 250 (tumor steps) occur in parallel with steps 215, 225, 235, 245, and 255 (graph steps). In one embodiment, the image associated with the tumor and the image associated with the benign area are separate images of tissue acquired from the same prostate. Since the image associated with the tumor and the image associated with the benign area are separate images, analysis of the images does not need to be conducted serially. Performing the tumor steps and benign steps in parallel may reduce the amount of time needed produce the set of TABS features. Faster prediction of CaP progression may enable application of treatments to CaP patients suffering from aggressive forms of CaP in a more clinically relevant time-frame than conventional methods.

Method 200 also includes, at 260, producing a set of TABS features. The set of TABS features includes the top ten most prognostically informative features from both the set of morphological features and the set of subgraph features. Method 200, at 260, selects the top ten most prognostically informative features from both the set of morphological features and the set of subgraph features. For example, method 200 may select three morphological features and seven subgraph features. In one embodiment, method 200 selects the TABS features using a Wilcoxon Rank Sum test. In another embodiment, the TABS features may be selected using a different test. In still another embodiment, the set of TABS features may include more or less than ten features.

Method 200 also includes, at 270, predicting CaP progression based, at least in part, on the set of TABS features. In one embodiment, predicting CaP progression includes calculating the probability that a tumor is a progressor or a non-progressor based, at least in part, on the set of TABS features and a GS for the tumor. Method 200 may control a CADx system to predict CaP progression based, at least in part, on the set of TABS features.

Figure 3:
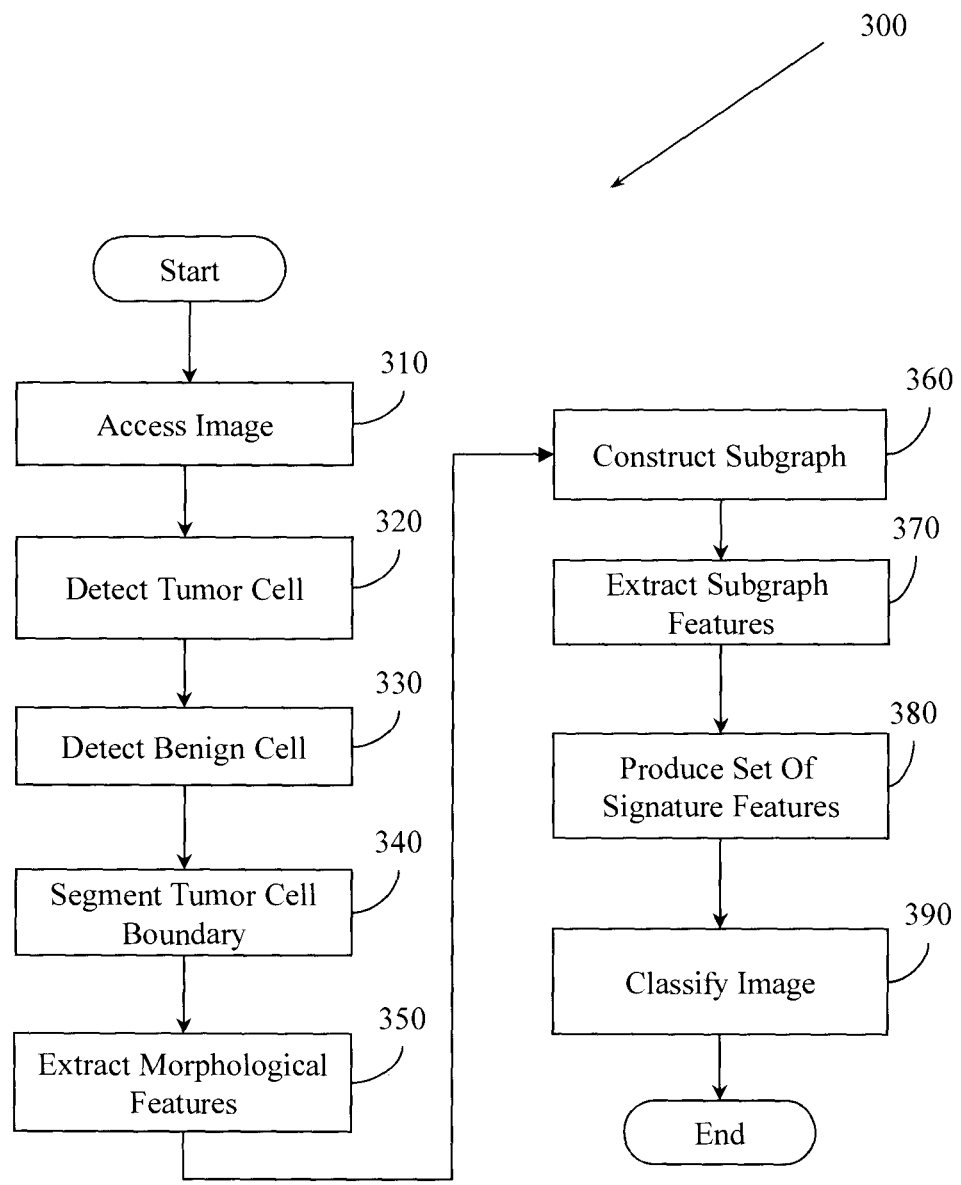
FIG. 3 illustrates an example method of identifying disease progression in a cancer patient.

FIG. 3 illustrates an example method 300 of identifying disease progression in a cancer patient. Method 300 includes, at 310, accessing an image of a section of tissue. The section of tissue includes a cancerous region and a benign region. The cancerous region is distinguishable from the benign region. In one embodiment, the image is a TMA image of a section of prostate exhibiting CaP. In another embodiment, the image may be an image of a section of breast cancer tissue, an image of a section of lung cancer tissue, or an image of a section of tissue exhibiting a type of cancer where the field effect describes a micro-environment around the site of a tumor that leads to a progression of the disease at another site.

Method 300 also includes, at 310, detecting a tumor cell in the cancerous region of the image. In one embodiment, method 300 uses a shape-based active contour segmentation scheme to detect the tumor cell. The shape-based active contour segmentation scheme includes an energy functional of the active contour. The energy functional may be a three-term functional. The energy functional may include a prior shape term modelled on tumor cell nuclei, a boundary-based term that detects the nuclear boundaries from image gradients, and a driving term that drives the shape prior and the contour towards the nuclear boundary based on region statistics. In another embodiment, a different scheme may be employed to detect the tumor cell.

Method 300 also includes, at 320, detecting a benign cell in the benign region of the image. In one embodiment, method 300 uses a shape-based active contour segmentation scheme to detect the benign cell. The shape-based active contour segmentation scheme includes an energy functional of the active contour. The energy function may be a three-term functional including a prior shape term modelled on benign cell nuclei, a boundary-based term that detects the nuclear boundaries from image gradients, and a driving term that drives the shape prior and the contour towards the nuclear boundary based on region statistics. In another embodiment, a different scheme may be used to detect the benign cell. In one embodiment, the shape-based active contour segmentation scheme used to detect a benign cell is the same shape-based active contour segmentation scheme used to detect a tumor cell. In another embodiment, different shape-based active contour segmentation schemes may be used.

Method 300 also includes, at 340, segmenting the boundary of the tumor cell into a set of boundary points using the shape-based active contour segmentation scheme.

Method 300 also includes, at 350, extracting a set of morphological features from the set of boundary points. The set of morphological features may be extracted from the set of boundary points segmented from the tumor cell. The set of morphological features are calculated from a set of statistics. In one embodiment, the set of statistics includes nuclear area and smoothness.

Method 300 also includes, at 360, constructing a subgraph of a localized cell network in the benign region. In one embodiment, the nodes of the subgraph represent individual cell nuclei centroids. The edges of the subgraph are defined between pairs of nodes by a probabilistic decaying function of the Euclidean distance between a first node and a second node. In one embodiment, the density of the subgraph is controllable by a user.

Method 300 also includes, at 370, extracting a set of subgraph features from the subgraph. The set of subgraph features describe the spatial organization of cell nuclei within the tissue represented in the benign image. The spatial organization of cell nuclei described by the set of subgraph features enables method 300 to use field effects detected in the benign region to predict cancer progression. In one embodiment, the set of subgraph features includes architectural features including Voronoi diagrams, Delaunay triangulations, Voronoi polygon area, Delaunay edge length, and nuclear density features. In another embodiment, a subgraph of the tumor region may also be constructed, and subgraph features from the subgraph of the tumor region may be extracted.

Method 300 also includes, at 380, producing a set of signature features. The set of signature features includes a subset of the set of morphological features and a subset of the set of subgraph features. In one embodiment, method 300 uses a Wilcoxon Rank Sum test to select the most prognostically informative subset of features from the set of morphological features and the set of subgraph features. In one embodiment, the set of signature features includes at least two features selected from the set of morphological features.

Method 300 also includes, at 390, classifying the section of tissue. Classifying the section of tissue includes controlling a computer aided diagnostic (CADx) system to classify the section of tissue as a progressor or a non-progressor. The classification is based, at least in part, on the set of signature features. In one embodiment, method 300 controls the CADx system to classify the section of tissue based on the set of signature features and a GS for the section of tissue. Classifying the section of tissue using both the set of signature features and the GS provides improved accuracy compared to conventional methods of predicting cancer progression that employ either Gleason scoring or a set of graph features, but not both.

Example methods and apparatus improve the prediction of cancer progression compared to conventional methods by using the TABS features instead of just features extracted from the cancerous region. The combined tumor and adjacent benign features included in the TABS feature set increase the accuracy of predicting cancer progression using automated QH compared to conventional methods. Employing the TABS feature set in combination with GS further improves on conventional methods. Example methods and apparatus leverage disconnected feature sets that are not exploited by conventional methods, which facilitates making more accurate predictions of patient prognosis. Improving patient prognosis prediction facilitates allocating resources, personnel, and therapeutics to appropriate patients while sparing other patients from treatment that might have been prescribed with a less accurate prediction.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, and method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 4:
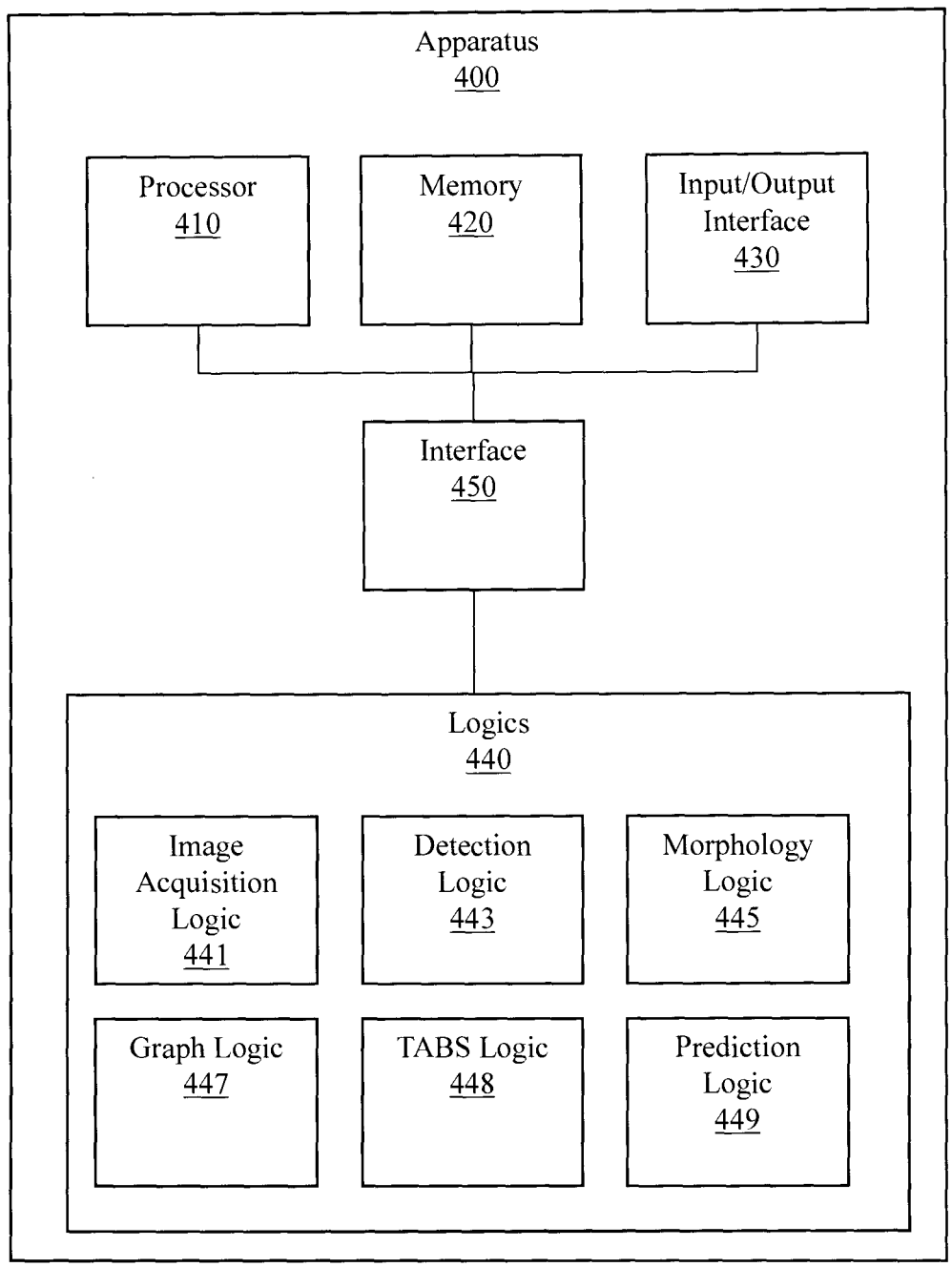
FIG. 4 illustrates an example apparatus that predicts cancer progression in a patient.

FIG. 4 illustrates an example apparatus 400 that predicts cancer progression in a patient. Apparatus 400 includes a processor 410, a memory 420, an input/output interface 430, a set of logics 440, and an interface 450 that connects the processor 410, the memory 420, the input/output interface 430, and the set of logics 440. The set of logics 440 includes an image acquisition logic 441, a detection logic 443, a morphology logic 445, a graph logic 447, a tumor plus adjacent benign signature (TABS) logic 448, and a prediction logic 449

Image acquisition logic 441 acquires an image of a region of tissue. The region of tissue may be a section of tissue demonstrating cancerous pathology in a patient. The image may be a 1670 pixel by 1670 pixel image of a 0.6 mm TMA core stained with H&E. The TMA core may be sampled from a cancerous region or from a benign region adjacent to the cancerous region. More generally, the image may be a digital image of a tissue slide. In one embodiment, image acquisition logic 441 acquires a digitally scanned H&E stained image from a digital stain scanner. In another embodiment, images that are made using other scanners, other staining techniques, other dimensions, or different magnification levels may be acquired. For example, the image may be provided by an optical microscope or an automated slide staining system. Thus, accessing the image may include interacting with a scanning apparatus, an optical microscope, or an automated slide staining system. Other imaging systems may be used to generate and access the image accessed by image acquisition logic 441.

Detection logic 443 detects and segments a cell boundary as a function of a shape-based active contour segmentation scheme. In one embodiment, the shape-based active contour segmentation scheme includes a three-term energy functional. The energy functional includes a shape prior term. The shape prior term constrains the deformation achievable by the active contour. The energy functional also includes a boundary-based term that detects cellular boundaries from image gradients. The energy functional also contains a driving term. The driving term drives the shape prior and the contour towards the cell boundary based, at least in part, on region statistics. In another embodiment, the boundary-based term detects nuclear boundaries or cellular boundaries, and the driving term drives the shape prior and contour towards the nuclear boundary or the cell boundary based, at least in part, on region statistics. In another embodiment, detection logic 443 detects and segments a cell boundary using a different segmentation scheme. The different segmentation scheme may have a different number of terms.

Morphology logic 445 extracts a set of morphological features from the set of cell boundary points. In one embodiment, morphology logic 445 extracts 173 features from the cell of cell boundary points. In one embodiment, morphology logic 445 selects at least a threshold number of the most prognostically significant features from the set of morphology features. In one embodiment, the threshold number is ten. In another embodiment, the threshold number may be more or less than ten. In one embodiment, morphology logic 445 selects the threshold number of features from the set of morphological features as a function of a Wilcoxon Rank Sum test. In another embodiment, morphology logic 445 may use a different test to select the most prognostically significant features.

Graph logic 447 constructs a graph of a localized cellular neighborhood detected in the benign region. Nodes in the graph represent nuclei in the region of tissue. The probability that a first node in the graph is connected to a second, different node in the graph is based on a probabilistic decaying function of the Euclidean distance between the first node and the second node. In one embodiment, the density of the graph is a function of the Euclidean distance between nodes and a user-controllable parameter. Graph logic 447 also extracts a set of graph features from the graph. The graph features include Voronoi polygon area, Delaunay edge length, or nuclear density features. In one embodiment, graph logic 447 extracts at least N graph features from the graph. In this embodiment, N is a number equal to or greater than 26. In another embodiment, N may have different values. For example, graph logic 447 may extract 173 features from the graph.

TABS logic 448 constructs a set of TABS features. The set of TABS features includes a subset of the set of morphological features and a subset of the set of subgraph features. In one embodiment, TABS logic 448 uses a Wilcoxon Rank Sum test to select at least a threshold number of the most prognostically significant features from the set of morphological features and the set of graph features. In one embodiment, the threshold number is at least ten. TABS logic 448 selects at least X graph features and at least Y morphological features to construct the set of TABS features. X and Y are numbers. In one embodiment, X is at least seven and Y is at least two.

Prediction logic 449 calculates the probability that a tumor represented in the image is a progressor or a non-progressor. Prediction logic 449 calculates the probability based, at least in part, on the set of TABS features. In one embodiment, prediction logic 449 calculates the probability based on both the set of TABS features and a Gleason scoring of the image. Calculating the probability based on both the set of TABS features and a Gleason scoring of the image results in apparatus 400 achieving an area under the curve value of at least 0.82 with a p-value of 0.0015. Apparatus 400 thus improves on conventional cancer prediction apparatuses which employ Gleason scoring or morphological features separately.

In another embodiment, prediction logic 449 may control a computer aided diagnosis (CADx) system to classify the image based, at least in part, on the probability that the tumor is a progressor or a non-progressor. For example, prediction logic 449 may control a computer aided CaP diagnostic system to grade the image based, at least in part, on the set of TABS features. In other embodiments, other types of CADx systems may be controlled, including CADx systems for grading colon cancer, lung cancer, bone metastases, breast cancer, and other diseases where disease progression may be predicted based on a set of TABS features. Prediction logic 449 may control the CADx system to display the prediction on a computer monitor, a smartphone display, a tablet display, or other displays. Displaying the prediction may also include printing the prediction. Prediction logic 449 may also control the CADx to display an image of the tumor region and an image of the benign region. The image of the tumor region may include the set of morphological features. The image of the benign region may include a visual representation of a graph of the localized cellular neighborhood in the benign region.

Figure 5:
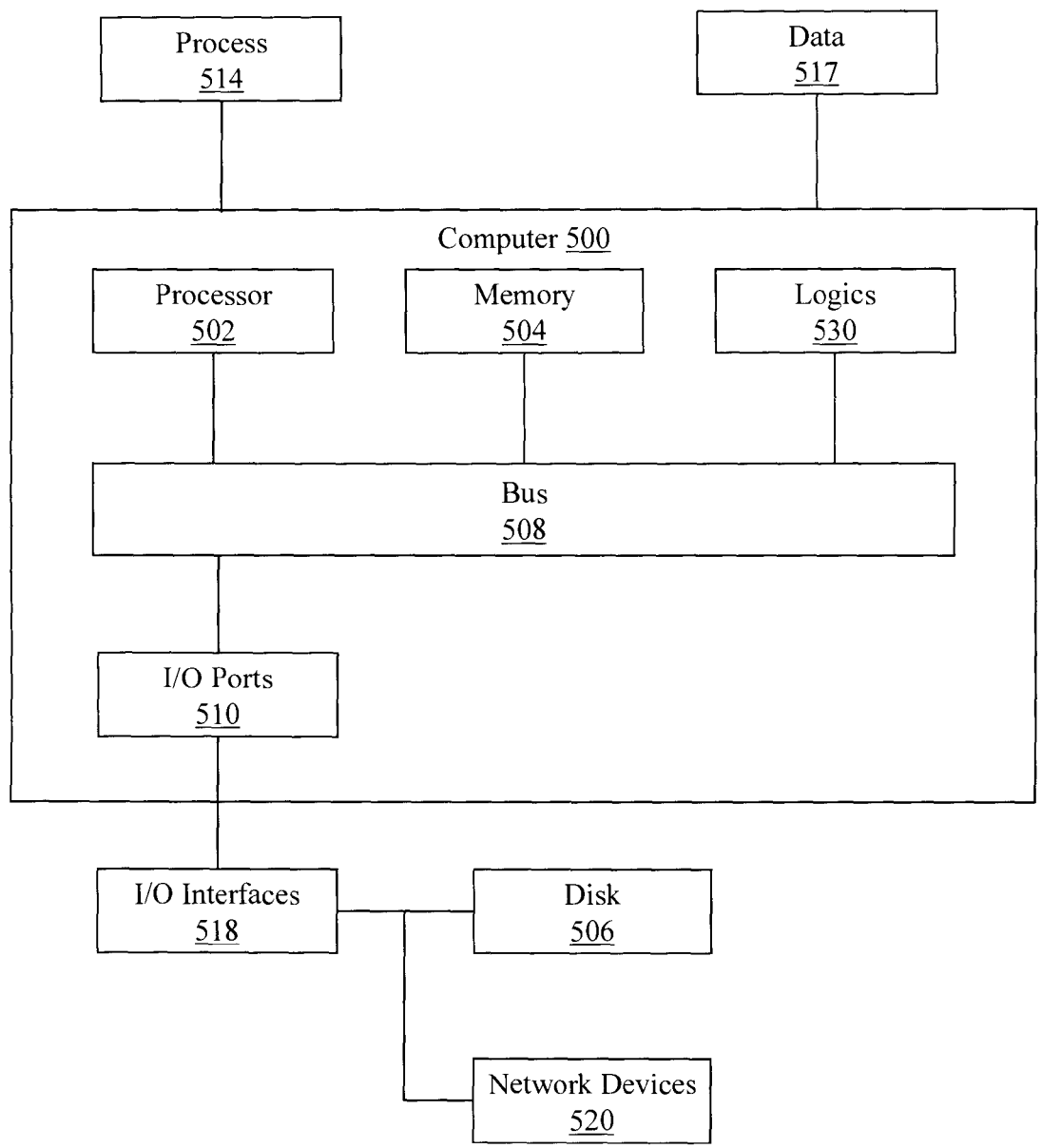
FIG. 5 illustrates an example computer in which example methods and apparatus described herein operate.

FIG. 5 illustrates an example computer 500 in which example methods illustrated herein can operate and in which example logics may be implemented. In different examples computer 500 may be part of a digital whole slide scanner, may be operably connectable to a digital whole slide scanner, may be part of a microscope, may be operably connected to a microscope, or may be part of a CADx system.

Computer 500 includes a processor 502, a memory 504, and input/output ports 510 operably connected by a bus 508. In one example, computer 500 may include a set of logics 530 that perform a method of predicting CaP progression in a cancer patient using field effects in automated QH. Thus, the set of logics 530, whether implemented in computer 500 as hardware, firmware, software, and/or a combination thereof may provide means (e.g., hardware, software) for predicting CaP progression in a cancer patient using field effects in automated QH. In different examples, the set of logics 530 may be permanently and/or removably attached to computer 500.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a flash memory card, or a memory stick. Furthermore, disk 506 may include optical drives like a CD-ROM or a digital video ROM drive (DVD ROM). Memory 504 can store processes 514 or data 517, for example. Disk 506 or memory 504 can store an operating system that controls and allocates resources of computer 500.

Bus 508 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital whole slide scanners, an optical microscope, a keyboard, a microphone, a pointing and selection device, cameras, video cards, displays, disk 506, network devices 520, or other devices. Input/output ports 510 can include but are not limited to, serial ports, parallel ports, or USB ports.

Computer 500 may operate in a network environment and thus may be connected to network devices 520 via I/O interfaces 518 or I/O ports 510. Through the network devices 520, computer 500 may interact with a network. Through the network, computer 500 may be logically connected to remote computers. The networks with which computer 500 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory, computer-readable storage medium storing computer executable instructions that when executed by a computer control the computer to perform a method for predicting prostate cancer (CaP) progression in a patient using field effects in automated quantitative histomorphometry (QH), the method comprising:
  accessing a first digital image of a tissue slide, where the first digital image includes a cancerous section of a prostate demonstrating pathology associated with CaP in the patient;
  detecting a first cell in a first region of interest of the first digital image;
  segmenting the boundary of the first cell into a set of cell boundary points;
  extracting a set of morphological features from the set of cell boundary points;
  accessing a second digital image of a tissue slide, where the second digital image includes a benign section of the prostate;
  detecting a second cell in a second region of interest in the second digital image;
  constructing a subgraph of a localized cell network within the second region of interest by linking individual cells located proximal to each other, where the nodes of the subgraph represent individual cell nuclei centroids, and where the edges of the subgraph are defined between pairs of cells by a probabilistic decaying function;
  extracting a set of subgraph features from the subgraph, where the set of subgraph features characterizes a field effect of the local cell organization;
  producing a set of tumor plus adjacent benign signature (TABS) features from the set of morphological features and the set of subgraph features; and
  controlling a computer to predict CaP progression in the patient, based, at least in part, on the set of TABS features.

2. The non-transitory computer-readable storage medium of claim 1, where the first digital image and the second digital image are at least 1670 pixel by at least 1670 pixel images of 0.6 mm tissue microarray cores stained with hematoxylin and eosin (H&E).

3. The non-transitory computer-readable storage medium of claim 1, where detecting the first cell and segmenting the boundary of the first cell is based on a shape-based active contour segmentation scheme, where the segmentation scheme includes an energy functional of the active contour.

4. The non-transitory computer-readable storage medium of claim 3, where the energy functional is defined as $$F = \beta_s \int_\Omega (\phi(x) - \psi(x))^2 |\nabla \phi| \delta(\phi) dx + \beta_r \int_\Omega \theta_{in} H_\psi dx + \int_\Omega \theta_{out} H_{-\psi} dx,$$

where $\beta_s \int_\Omega (\phi(x) - \psi(x))^2 |\nabla \phi| \delta(\phi) dx$ represents a shape plus boundary force,
  $\beta_r \int_\Omega \theta_{in} H_\psi dx + \int_\Omega \theta_{out} H_{-\psi} dx$ represents a region force,
  $\beta_s, \beta_r > 0$ are constants that balance contributions of the shape plus boundary force and the region force,
  $\{\phi\}$ is a level set function,
  $\psi$ is a shape prior,
  $\delta(\phi)$ is a contour measure on $\{\phi = 0\}$,
  H(.) is the Heaviside function, $$\theta_r = |I - u_r|^2 + \mu |\nabla u_r|^2,$$

r∈{in, out},
  $u_r$ is defined such that r∈{in, out} are partitioned foreground and background regions, and
  $\Omega$ is a bounded open set in $\mathbb{R}^2$.

5. The non-transitory computer-readable storage medium of claim 4, where the shape plus boundary force represents a prior shape term modeled on a prostate nuclei, where the shape plus boundary force constrains a deformation achievable by the active contour.

6. The non-transitory computer-readable storage medium of claim 4, where the region force comprises a boundary-based term $\beta_r \int_\Omega \theta_{in} H_\psi dx$, and a third term $\int_\Omega \theta_{out} H_{-\psi} dx$, where the boundary-based term detects a nuclear boundary from an image gradient, and the third term drives the shape prior and the contour towards the nuclear boundary based, at least in part, on a set of region statistics.

7. The non-transitory computer-readable storage medium of claim 6, where extracting the set of morphological features from the set of cell boundary points comprises calculating at least 100 morphological features based, at least in part, on nuclear area and smoothness.

8. The non-transitory computer-readable storage medium of claim 1, where the probabilistic decaying function is defined as $$E = \{(i,j) : r < D(i,j)^{-\alpha}, \forall n_i, n_j \in V\},$$

where $D(i,j)$ represents the Euclidean distance between a first node $n_i$ and a second node $n_j$, where $\alpha \geq 0$ controls the density of the subgraph, and where $r \in [0,1]$ is an empirically determined edge threshold.

9. The non-transitory computer-readable storage medium of claim 8, where the set of subgraph features includes at least 26 features, and where the 26 features include eccentricity and connected component size.

10. The non-transitory computer-readable storage medium of claim 9, the method comprising selecting at least a threshold number of the most prognostically informative subgraph features for predicting CaP progression from the set of subgraph features.

11. The non-transitory computer-readable storage medium of claim 10, where the threshold number is 10.

12. The non-transitory computer-readable storage medium of claim 10, comprising selecting the threshold number of the most prognostically informative subgraph features using a Wilcoxon Rank Sum test.

13. The non-transitory computer-readable storage medium of claim 10, the method comprising selecting at least a threshold number of the most prognostically informative morphological features for predicting CaP progression from the set of morphological features.

14. The non-transitory computer-readable storage medium of claim 13, where the threshold number is 10.

15. The non-transitory computer-readable storage medium of claim 14, comprising selecting at least the threshold number of the most prognostically informative morphological features using a Wilcoxon Rank Sum test.

16. The non-transitory computer-readable storage medium of claim 15, where producing the set of TABS features comprises selecting at least a threshold number of the most prognostically informative features for predicting CaP progression from the set of morphological features and from the set of subgraph features.

17. The non-transitory computer-readable storage medium of claim 16, where the threshold number is 10.

18. The non-transitory computer-readable storage medium of claim 17, comprising selecting the set of TABS features using a Wilcoxon Rank Sum test.

19. The non-transitory computer-readable storage medium of claim 18, where the set of TABS features includes at least 7 subgraph features extracted from the benign region, at least 1 morphological feature extracted from the cancerous region, at least 1 Delaunay triangulation feature extracted from the cancerous region, and at least 1 morphological feature extracted from the benign region.

20. The non-transitory computer-readable storage medium of claim 1, where controlling a computer to predict CaP progression in the patient comprises calculating a Gleason Sum for the patient, and predicting CaP progression based on the set of TABS features and the Gleason Sum.

21. A non-transitory computer-readable storage medium storing computer-executable instructions that when executed by a computer control the computer to perform a method for identifying disease progression in a cancer patient, the method comprising:

accessing an image of a section of tissue, where the section of tissue includes a cancerous region and a benign region, where the cancerous region is distinguishable from the benign region;

detecting a tumor cell in the portion of the image associated with the cancerous region;

detecting a benign cell in the portion of the image associated with the benign region;

segmenting the boundary of the tumor cell into a set of boundary points;

extracting a set of morphological features from the set of boundary points;

constructing a subgraph of a localized cell network in the portion of the image associated with the benign region, where the nodes of the subgraph represent individual cell nuclei centroids, where the edges of the subgraph are defined between pairs of cells by a probabilistic decaying function;

extracting a set of subgraph features from the subgraph;

producing a set of signature features, where the set of signature features includes a subset of the set of morphological features and a subset of the set of subgraph features; and controlling a computer aided diagnostic system (CADx) to classify the section of tissue as a progressor or a non-progressor, based, at least in part, on the set of signature features.

22. An apparatus for predicting cancer progression in a patient, comprising:

a processor;

a memory;

an input/output interface;

a set of logics; and an interface to connect the processor, the memory, the input/output interface and the set of logics, the set of logics comprising:

an image acquisition logic that acquires an image of a region of tissue, where the region of tissue includes a tumor region and a benign region, where the benign region is distinguishable from the tumor region;

a detection logic that detects a cell in the image and segments the cell boundary of the cell into a set of cell boundary points;

a morphology logic that extracts a set of morphological features from the set of cell boundary points;

a graph logic that constructs a graph of a localized cellular neighborhood in the benign region and extracts a set of graph features from the graph;

a tumor plus adjacent features signature (TABS) logic that constructs a set of TABS features from the set of morphological features and the set of graph features; and a prediction logic that calculates the probability that a tumor represented in the image is a progressor or non-progressor based, at least in part, on the set of TABS features.

23. The apparatus of claim 22, where the detection logic detects and segments a cell boundary as a function of a shape-based active contour segmentation scheme comprising an energy functional, where the energy functional comprises a shape prior term that constrains the deformation achievable by the active contour, a boundary-based term that detects cellular boundaries from image gradients, and a driving term that drives the shape prior and the contour towards the cell boundary based, at least in part, on region statistics.

24. The apparatus of claim 23, where the morphology logic selects at least a threshold number of the most prognostically significant features from the set of morphological features as a function of a Wilcoxon Rank Sum test.

25. The apparatus of claim 24, where the threshold number is at least 10.

26. The apparatus of claim 25, where the graph logic extracts at least N graph features from the graph including Voronoi polygon area, Delaunay edge length, or nuclear density features, where N is a number, and where the probability that a first node in the graph is connected by an edge to a second node in the graph is based on a probabilistic decaying function of the Euclidean distance between the first node and the second node.

27. The apparatus of claim 26, where N is at least 26.

28. The apparatus of claim 27, where the TABS logic constructs a set of TABS features using a Wilcoxon Rank Sum test to select at least a threshold number of the most prognostically significant features from the set of morphological features and the set of graph features, where the set of TABS features includes at least X graph features and at least Y morphological features, where X is a number and where Y is a number.

29. The apparatus of claim 28, where the threshold number is 10.

30. The apparatus of claim 29, where X is 7 and Y is 2.

* * * * *